United States Patent [19]

Chen

[11] Patent Number: 5,239,723
[45] Date of Patent: Aug. 31, 1993

[54] GELATINOUS ELASTOMER SWABS

[75] Inventor: John Y. Chen, Pacifica, Calif.

[73] Assignee: Applied Elastomerics, Inc., Pacifica, Calif.

[21] Appl. No.: 934,027

[22] Filed: Aug. 24, 1992

Related U.S. Application Data

[63] Continuation-in-part of Ser. No. 705,711, May 23, 1991, which is a continuation-in-part of Ser. No. 211,426, Jun. 24, 1988, Pat. No. 5,153,254, which is a continuation-in-part of Ser. No. 921,752, Oct. 21, 1986, abandoned, which is a continuation-in-part of Ser. No. 572,172, Jan. 18, 1984, Pat. No. 4,618,213, which is a continuation-in-part of Ser. No. 458,703, Jan. 17, 1983, abandoned, which is a continuation-in-part of Ser. No. 134,977, Mar. 28, 1980, Pat. No. 4,369,284, which is a continuation-in-part of Ser. No. 916,731, Jun. 19, 1978, abandoned, which is a continuation-in-part of Ser. No. 815,315, Jul. 13, 1977, abandoned, which is a continuation-in-part of Ser. No. 778,343, Mar. 17, 1977, abandoned.

[51] Int. Cl.$^5$ .................. A47L 25/00; A47L 25/08; A47L 13/08
[52] U.S. Cl. .................. 15/104.002; 15/210.1; 15/214; 524/474; 524/476; 524/505
[58] Field of Search .............. 15/104.002, 210.1, 214; 524/505, 474, 476

[56] References Cited

U.S. PATENT DOCUMENTS

| | | |
|---|---|---|
| 3,485,787 | 12/1969 | Haefele . |
| 3,676,387 | 7/1972 | Lindlof . |
| 3,827,999 | 8/1974 | Crossland . |
| 3,906,578 | 9/1975 | Huber ............................ 428/132 |
| 4,104,822 | 8/1978 | Rodgers ............................ 446/48 |
| 4,151,057 | 4/1979 | St. Clair . |
| 4,176,240 | 11/1979 | Sabia ............................ 524/474 |
| 4,259,540 | 3/1981 | Sabia . |
| 4,351,913 | 9/1982 | Patel . |
| 4,369,284 | 1/1983 | Chen ............................ 524/505 |
| 4,399,579 | 8/1983 | McKay ............................ 15/104 A |
| 4,432,607 | 2/1984 | Levy . |
| 4,466,212 | 8/1984 | Lehman ............................ 446/46 |
| 4,492,270 | 7/1990 | Gamarra ............................ 174/93 |
| 4,492,428 | 1/1985 | Levy . |
| 4,497,538 | 2/1985 | Patel . |
| 4,509,821 | 4/1985 | Stenger . |
| 4,516,946 | 5/1985 | Rodarte ............................ 446/46 |
| 4,516,947 | 5/1985 | Pircher ............................ 446/46 |
| 4,546,517 | 10/1985 | Caniglia ............................ 15/214 |
| 4,600,261 | 7/1986 | Debbaut . |
| 4,610,738 | 9/1986 | Jervis . |
| 4,618,213 | 10/1986 | Chen ............................ 524/505 |
| 4,662,692 | 5/1987 | Uken . |
| 4,680,233 | 7/1987 | Camin . |
| 4,687,095 | 8/1987 | Iwasaki ............................ 15/104 A |
| 4,690,831 | 9/1987 | Uken . |
| 4,709,982 | 12/1987 | Corne ............................ 350/96.23 |
| 4,716,183 | 12/1987 | Gamarra . |
| 4,764,535 | 8/1988 | Leicht . |

(List continued on next page.)

FOREIGN PATENT DOCUMENTS 1268431 of 0000 United Kingdom .

OTHER PUBLICATIONS

SC:1102-89 Shell Chemical Technical Bulletin "KRATON ® Thermoplastic Rubber in oil gels".

Primary Examiner—Herbert J. Lilling

[57] ABSTRACT

A novel reusable swab having a gelatinous elastomer swab head attached to one or both ends of a handle is disclosed. The gelatinous elastomer swab head exhibits a combination of properties including unexpectedly high elongation and tensile strength and excellent shape retention after extreme deformation under high-velocity impact and stress conditions. The gelatinous elastomer swabs of this invention are soft, flexible, and have elastic memory, characterized by a gel rigidity of from about 20 gram to about 800 gram Bloom. These and other properties are particularly essential for cleaning various surfaces, deeply recessed areas small crevices, curved surfaces, various hard-to-clean corners of a car interior, other nooks and crannies, and the like.

6 Claims, 1 Drawing Sheet

U.S. PATENT DOCUMENTS

| | | |
|---|---|---|
| 4,801,346 | 1/1989 | Huddleston . |
| 4,822,834 | 4/1989 | Blevins . |
| 4,833,193 | 5/1989 | Sieverding . |
| 4,864,677 | 9/1989 | Levy .................. 15/210 R |
| 4,865,905 | 9/1989 | Uken . |
| 4,883,431 | 11/1989 | Uken . |
| 4,888,070 | 12/1989 | Clark . |
| 4,889,403 | 12/1989 | Zucker . |
| 4,900,877 | 2/1990 | Drbrow ................. 174/35 |
| 4,905,337 | 3/1990 | McKay ..................... 15/104 A |
| 4,909,756 | 3/1990 | Jervis . |
| 4,920,662 | 5/1970 | Seeburger ..................... 34/60 |
| 4,940,441 | 7/1970 | Novinsky ..................... 446/46 |
| 4,942,270 | 7/1990 | Gamarra . |
| 4,944,363 | 7/1990 | Osher ..................... 273/58 |
| 4,944,707 | 7/1990 | Silverglate ..................... 446/48 |
| 4,944,973 | 7/1990 | Follette . |
| 4,975,997 | 12/1990 | Levy ..................... 15/210 R |
| 5,026,054 | 6/1991 | Osher et al. ..................... 273/58 A |
| 5,153,254 | 10/1992 | Chen ..................... 524/505 |

GELATINOUS ELASTOMER SWABS

REFERENCE TO RELATED APPLICATIONS AND PATENTS

This application is copending with application Ser. No. 876,118 filed Apr. 29, 1992 and application Ser. No. 705,096 filed May 23, 1991. This application is also a continuation-in-part of copending application Ser. No. 705,711 filed May 23, 1991 which is a continuation-in-part application Ser. No. 211,426 filed Jun. 24, 1988 now U.S. Pat. No. 5,153,25 which is a continuation-in-part application Ser. No. 921,752 filed Oct. 21, 1986 now abandoned, which is a continuation-in-part application Ser. No. 572,172, filed Jan. 18, 1984 and issued as U.S. Pat. No. 4,618,213 on Oct. 21, 1986, which is a continuation-in-part of application Ser. No. 458,703, filed Jan. 17, 1983 now abandoned, which is a continuation-in-part of application Ser. No. 134,977, filed Mar. 28, 1980 and issued as U.S. Pat. No. 4,369,284 on Jan. 18, 1983, which in turn is a continuation-in-part of application Ser. No. 916,731, filed Jun. 19, 1978 now abandoned, which is a continuation-in-part of application Ser. No. 815,315, filed Jul. 13, 1977 now abandoned, which is a continuation-in-part of application Ser. No. 778,343, filed Mar. 17, 1977 now abandoned. The subject matter contained in the related applications and patents are specifically incorporated herein by reference.

FIELD OF THE INVENTION

The present invention relates to swabs, more particular to cleaning swabs with novel swab heads.

BACKGROUND OF THE INVENTION

Cleaning swabs are well known in the art. These include swabs with heads made from various materials, such as knitted polyester, nonwoven polyester, foam, foam with a cotton bud core, nylon, and synthetic fibers (polyvinylidene Difluoride). They are also made in various shapes, such as single head or dual head, tape head, rectangular head, circular head, cube head, elongated head, small head, medium, head, large head, etc. Some swab heads are premoistened with 91% isopropanol or with a reusable reservoir of 91% isopropanol. The best known swab head material is cotton. For difficult to access areas requiring cleaning, the prior art swab heads do not work very well. A micro-vacuum or a pressurized spray of liquid or gas are often used to clean hard to reach areas. The micro-vacuum is costly and noisy. The liquid (evaporating) spray is often times messy, potentially explosive, and harmful to both man and environment.

SUMMARY OF THE INVENTION

I have invented swabs with novel heads for cleaning various surfaces and arresting lint. The swabs of the invention comprise a handle and a gelatinous elastomer head attached to one or both ends of the handle. The novel swab heads are made from a gelatinous elastomer composition having a gel rigidity of about 5 gram to about 800 gram Bloom.

The various aspects and advantages of the invention will become apparent to those skilled in the art upon consideration of the accompanying disclosure and the drawings.

DESCRIPTION OF THE PREFERRED EMBODIMENTS

Figure 1:
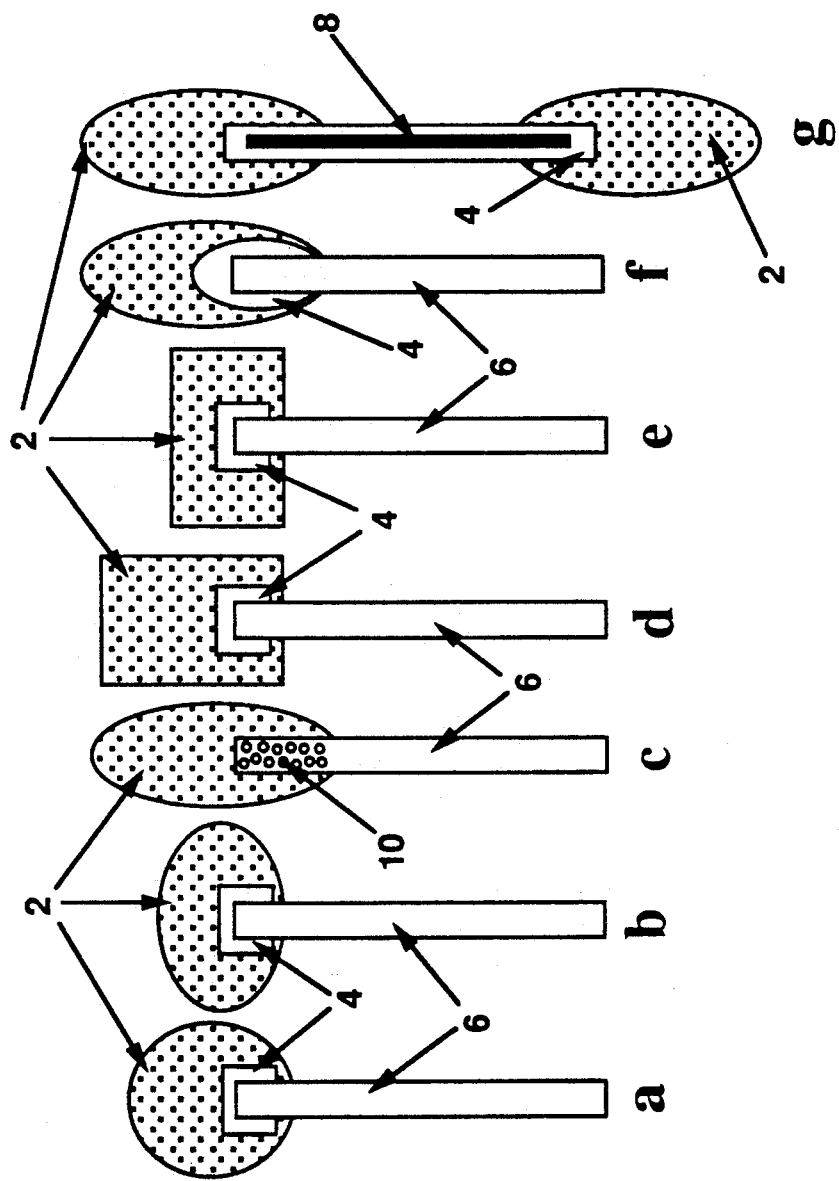
FIG. 1. Representative sectional views of various swabs of the invention.

Applicant's related patent application Ser. No. 211,426, filed Jun. 24, 1988 describe gel swabs. The gelatinous elastomer swabs of the invention are useful as novel reusable lint removers for cleaning the computer means, computer and typewriter keyboards, printers, copiers, camera lenses, LP records, various hard-to-clean corners of a car interior, and other nooks and crannies on the surface or inside buildings, houses, schools, ships, offices, and etc. Generally, the gelatinous elastomer swabs of the invention can be used to cleaned broad, flat surfaces, small areas, deeply recessed areas, small critical areas, small crevices, curved surfaces, and the like.

The gelatinous elastomer swab heads 2 have various additional important advantages in that they do not crack, creep, tear, crack, or rupture in flextural, tension, compression, or other deforming conditions of normal use; but rather the gelatinous elastomer swab heads 2 posses the intrinsic properties of elastic memory enabling the shaped gelatinous elastomer swab heads 2 to recover and retain its original shape after many extreme deformation cycles. In cleaning applications where low rigidity, high elongation, good compression set and excellent tensile strength are important, the gelatinous elastomer swab heads 2 have no equal. Moreover, the gelatinous elastomer swabs are washable and reusable.

The high viscosity triblock copolymers employed in forming the gelatinous elastomer swabs of the present invention have the more general configuration A-B-A wherein each A is a crystalline polymer end block segment of polystyrene; and B is a elastomeric polymer center block segment of poly(ethylene-butylene). The poly(ethylene-butylene) and polystyrene portions are incompatible and form a two-phase system consisting of sub-micron domains of glassy polystyrene interconnected by flexible poly(ethylene-butylene) chains. These domains serve to crosslink and reinforce the structure. This physical elastomeric network structure is reversible, and heating the polymer above the softening point of polystyrene temporarily disrupt the structure, which can be restored by lowering the temperature. Most recent reviews of triblock copolymers are found in the "ENCYCLOPEDIA OF POLYMER SCIENCE AND ENGINEERING", Volume 2 and 5, 1987–1988; "Thermoplastic Elastomers", MODERN PLASTIC ENCYCLOPEDIA, 1989; and Walker, B. M., Ed., et al., HANDBOOK OF THERMOPLASTIC ELASTOMERS, Van Nostrand Reinhold Co., 2nd Edition, 1988. These publications are incorporated herein by reference.

The shape of the gelatinous elastomer swab heads 2 of the invention can be any shape so long as it is suitable for use as a swab. For example, the gelatinous elastomer swab head can be in the form of a sphere, a cube, a rectangular parallelepiped, a prism, a truncated triangular prism, a pyramid, a frustum of pyramid, a prismatoid, a polyhedra, a right circular cylinder, a cone, a frustum of cone, a lune, a spherical sector, a ellipsoid, a bolate spheroid, a prolate spheroid, etc.

A gelatinous elastomer swab head 2 with an original molded shape can be deformed into another shape (to contact a regular or irregular surface) by pressure and upon removal of the applied pressure, the gelatinous elastomer swab head in the deformed shape will recover back to its original shape. Likewise, a thick shaped gelatinous elastomer swab head 2 can be deformed (stretched) into a thinner shaped head 2 just by contacting the gelatinous elastomer swab head 2 onto any surface containing lint; the lint is left-out by the gelatinous elastomer swab head 2 regardless of its shape.

The gelatinous elastomer swab heads 2 of the invention are formed from a composition by melt blending an admixture consisting essentially of: (A) 100 parts by weight of a high viscosity triblock copolymer of the general configuration poly(styrene-ethylene-butylene-styrene) where said triblock copolymer is characterized as having a Brookfield Viscosity of a 20 weight percent solids solution of said triblock copolymer in toluene at 25° C. of at least about 1,800 cps; (B) from about 300 to about 1,600 parts by weight of an plasticizing oil. Typically, the Brookfield Viscosity values of (A) can range from about 1,800 cps to about 16,000 cps. Less typically, the Brookfield Viscosity values of (A) can range from about 1,800 cps to about 30,000 cps or higher. The proportion of hydrocarbon plasticizing oil in (B) is more preferably from about 350 to about 1,600 parts per 100 parts of the triblock copolymer.

The high viscosity triblock copolymer of the invention can have a broad range of styrene end block to ethylene and butylene center block ratio of approximately about 20:80 or less to about 40:60 or higher. Examples of high viscosity triblock copolymers that can be utilized to achieve one or more of the novel properties of the present invention are styrene-ethylene-butylene-styrene block copolymers (SEBS) available from Shell Chemical Company and Pecten Chemical Company (divisions of Shell Oil Company) under trade designations Kraton G 1651, Kraton G 4600, Kraton G 4609 and the like. Other grades of (SEBS) polymers can also be utilized in the present invention provided such SEBS polymers exhibits the required high viscosity. Such SEBS polymers include (high viscosity) Kraton G 1855X which has a Specific Gravity of 0.92, Brookfield Viscosity of a 25 weight percent solids solution in toluene at 25° C. of about 40,000 cps or about 8,000 to about 20,000 cps at a 20 weight percent solids solution in toluene at 25° C.

The styrene to ethylene and butylene weight ratios for these Shell designated polymers can have a low range of 20:80 or less. Although the typical ratio values for Kraton G 1651, 4600, and 4609 are approximately about 33:67 and for Kraton G 1855X approximately about 27:73, these ratios can vary broadly from the typical product specification values. The styrene to ethylene and butylene weight ratio of SEBS useful in forming the gelatinous elastomer swab heads 2 can range from lower than about 20:80 to above about 40:60. More specifically, the values can be 19:81, 20:80, 21:79. 22:78. 23:77, 24:76, 25:75, 26:74, 27:73, 28:72, 29:71, 30:70, 31:69, 32:68, 33:67, 34:66, 35:65, 36:64, 37:63, 38:62, 39:61, 40:60, 41:59, 42:58, 43:57, 44:65, 45:55, 46:54, 47:53, 48:52, 49:51, 50:50, 52:49 and higher. Other ratio values of less than 19:81 or higher than 52:49 are also possible. Broadly, the styrene end block to ethylene and butylene center block ratio of the triblock copolymers of the invention is about 20:80 to about 40:60, less broadly about 31:69 to about 40:60, preferably about 32:68 to about 38:62, more preferably about 32:68 to about 36:64, particularly more preferably about 32:68 to about 34:66, especially more preferably about 33:67 to about 36:64, and most preferably about 33:67. In accordance with the present invention, triblock copolymers having ratios below 31:69 may be used, but they are less preferred due to their decrease in the desirable properties of the final composition.

Plasticizers particularly preferred for use in practicing the present invention are well known in the art, they include rubber processing oils such as paraffinic and naphthenic petroleum oils, highly refined aromatic-free paraffinic and naphthenic food and technical grade while petroleum mineral oils, and synthetic liquid oligomers of polybutene, polypropene, polyterpene, etc. The synthetic series process oils are high viscosity oligomers which are permanently fluid liquid nonolefins, isoparaffins or paraffins of moderate to high molecular weight. Many such oils are known and commercially available. Examples of representative commercially oils include Amoco ® polybutenes, hydrogenated polybutenes and polybutenes with epoxide functionality at one end of the polybutene polymer: Example of such polybutenes include: L-14 (320 $M_n$), L-50 ($M_n$), L-100 (460 $M_n$), H-15 (560 $M_n$), H-25 (610 $M_n$), H-35 (660 $M_n$), H-50 (750 $M_n$), H-100 (920 $M_n$), H-300 (1290 $M_n$), L-14E (27–37 cst @ 100° F. Viscosity), L-300E (635–690 cst @ 210° F. Viscosity), Actipol E6 (365 $M_n$), E16 (973 $M_n$), E23 (1433 $M_n$) and the like. Example of various commercially oils include: ARCO Prime and Tufflo oils, other while mineral oils include: Bayol, Bernol, American, Blandol, Brakeol, Ervol, Gloria, Kaydol, Kitetek, Marcol, Pariol, Peneteck, Primol, Protol, Sontex, and the like.

The high viscosity triblock copolymer component by itself lacks the desired properties; whereas, when the triblock copolymer (having Brookfield Viscosities of a 20 weight percent solids solution in toluene at 25° C. of about 1,800 cps or higher and styrene to ethylene and butylene ratio preferably of the range contemplated in the instant invention) is combined with selected plasticizing oils with an average molecular weight preferably of about 200 to about 700, as determined by ebullioscopic methods, wherein, for most purposes, the oil constitutes about 300 to about 1,600 parts and more preferably about 350 to about 1,600 parts by weight of the triblock copolymer, that an extremely soft and highly elastic material is obtained. This transformation of the triblock copolymer structure in heated oil resulting in a composition having a gel rigidity preferably of about 20 gram or lower to about 800 gram Bloom and substantially without oil bleedout along with high tensile strength and elongation and other desirable combination of physical properties is unexpected. As used herein, the term "gel rigidity" in gram Bloom is determined by the gram weight required to depress a gel a distance of 4 mm with a piston having a cross-sectional area of 1 square centimeter at 23° C.

In accordance with the practice of the present invention, the aforementioned molecular weight range plasticizing oils are most preferred. Generally, plasticizing oils with average molecular weights less than about 200 and greater than about 700 may also be used.

The composition utilized for the gelatinous elastomer swab heads 2 can also contain useful amounts of conventionally employed additives such as stabilizers, antioxidants, antiblocking agents, colorants, fragrances, flame retardants, other polymers in minor amounts and the like to an extend not affecting or substantially decreasing the desired properties of the present invention.

Additives useful in the composition of the present invention include: tetrakis[methylene 3,-(3'5'-di-tertbutyl-4"-hydroxyphenyl) propionate] methane, octadecyl 3-(3", 5"-di-tert-butyl-4"-hydroxyphenyl) propionate, distearyl- pentaerythritoldiproprionate, thiodiethylene bis-(3,5-ter-butyl-4-hydroxy) hydrocinnamate, (1,3,5-trimethyl-2,4,6-tris[3,5-di-tert-butyl-4-hydroxybenzyl] benzene), 4,4"-methylenebis(2,6-di-tert-butylphenol), steraric acid, oleic acid, stearamide, behenamide, oleamide, erucamide, N,N"-ethylenebisstearamide, N,N"-ethylenebisoleamide, sterryl erucamide, erucyl erucamide, oleyl palmitamide, stearyl stearamide, erucyl stearamide, waxes (e.g. polyethylene, polypropylene, microcrystalline, carnauba, paraffin, montan, candelilla, beeswax, ozokerite, ceresine, and the like). Minor amounts of other polymers and copolymers can be melt blended with the styrene-ethylene-butylene-styrene block copolymers mentioned above without substantially decreasing the desired properties. Such polymers include (SBS) styrene-butadiene-styrene block copolymers, (SIS) styrene-isoprene-styrene block copolymers, (low styrene content SEBS) styrene-ethylene-butylene-styrene block copolymers, (SEP) styrene-ethylene-propylene block copolymers, (SB)n styrene-butadiene and (SEB)n, (SEBS)n, (SEP)n, (Si)n styrene-isoprene multi-arm, branched, and star shaped copolymers and the like. Still, other homopolymers can be utilized in minor amounts; these include: polystyrene, polybutylene, polyethylene, polypropylene and the like. The composition can also contain metallic pigments (aluminum and brass flakes), $TiO_2$, mica, fluorescent dyes and pigments, phosphorescent pigments, aluminatrihydrate, antimony oxide, iron oxides ($Fe_3O_4$, $-Fe_2O_3$, etc.), iron cobalt oxides, chromium dioxide, iron, barium ferrite, strontium ferrite and other magnetic particle materials, molybdenum, silicone fluids, lake pigments, aluminates, ceramic pigments, ironblues, ultramarines, phthalocynines, azo pigments, carbon blacks, silicon dioxide, silica, clay, feldspar, glass microspheres, barium ferrite, wollastonite and the like. The report of the committee on *Magnetic Materials,* Publication NMAB-426, National Academy Press (1985) is incorporated herein by reference.

The gelatinous elastomer compositions of the present invention are prepared by blending together the components including other additives as desired at about 23° C. to about 100° C. forming a paste like mixture and further heating said mixture uniformly to about 150° C. to about 200° C. until a homogeneous molten blend is obtained. Lower and higher temperatures can also be utilized depending on the viscosity of the oils and amount of SEBS used. These components blend easily in the melt and a heated vessel equipped with a stirrer is all that is required. Small batches can be easily blended in a test tube using a glass stirring rod for mixing. While conventional large vessels with pressure and/or vacuum means can be utilized in forming large batches of the instant compositions in amounts of about 40 lbs or less to 10,000 lbs or more. For example, in a large vessel, inert gases can be employed for removing the composition from a closed vessel at the end of mixing and a partial vacuum can be applied to remove any entrapped bubbles. Stirring rates utilized for large batches can range from about less than 10 rpm to about 40 rpm or higher.

The basis of the gelatinous compositions forming the novel gelatinous elastomer swab heads 2 of this invention resides in the fact that a high viscosity poly(styrene-ethylene-butylene-styrene) triblock copolymer having styrene end block to ethylene and butylene center block ratio preferably within the contemplated range of from about 20:80 to about 40:60, more preferably from between about 31:69 to about 40:60 when blended in the melt with an appropriate amount of plasticizing oil makes possible the attainment of gelatinous elastomer compositions having a desirable combination of physical and mechanical properties, notably high elongation at break of at least 1,600%, ultimate tensile strength of about at least $8 \times 10^5$ dyne/$cm^2$, low elongation set at break of substantially not greater than about 2%, tear resistance of at least $5 \times 10^5$ dyne/$cm^2$, substantially about 100% snap back when extended to 1,200% elongation, and a gel rigidity of substantially not greater than about 800 gram Bloom. It should be noted that when the ratio falls below 31:69, various properties such as elongation, tensile strength, tear resistance and the like can decrease while retaining other desired properties, such as gel rigidity, flexibility, elastic memory.

More specifically, the gelatinous elastomer composition forming the swabs of the present invention exhibit one or more of the following properties. These are: (1) tensile strength of about $8 \times 10^5$ dyne/$cm^2$ to about $10^7$ dyne/$cm^2$; (2) elongation of about 1,600% to about 3,000% and higher; (3) elasticity modulus of about $10^4$ dyne/$cm^2$ to about $10^6$ dyne/$cm^2$; (4) shear modulus of about $10^4$ dyne/$cm^2$ to about $10^6$ dyne/$cm^2$ as measured with a 1, 2 and 3 kilogram load at 23° C.; (5) gel rigidity of about 20 gram Bloom or lower to about 800 gram Bloom as measured by the gram weight required to depress a gel a distance of 4 mm with a piston having a cross-sectional area of 1 square cm at 23° C.; (6) tear propagation resistance of at least about $5 \times 10^5$ dyne/$cm^2$; (7) and substantially 100% snap back recovery when extended at a cross head separation speed of 25 cm/minute to 1,200% at 23° C. Properties (1), (2), (3), and (6) above are measured at a crosshead separation speed of 25 cm/minute at 23° C.

The gelatinous elastomer composition of the invention is excellent for forming the gelatinous elastomer swab heads 2 of the invention. The gelatinous elastomer swab heads 2 can be formed by blending, melting, dipping, casting, injection molding, extruding and other conventional methods. The composition can also be remelted in any suitable hot melt applicator for hot dipping, extrusion, sputtering, or spraying on to the handles 6 so as to form the gelatinous elastomer swab heads 2 of the swabs of the invention.

The gelatinous elastomer swab head 2 can be conductive or non-conductive, containing conductive fillers (carbon, metal flakes etc.) or non-conductive fillers. The gelatinous elastomer swab heads 2 can be formed in combination with other materials, such as open cell foams, other polymeric or elastomeric (Kraton) materials, porous materials, multi-layered coatings, signal layered, composite layered materials. As an example, an opened cell foam when dipped into the instant composition will form an interpentrating physical networks (interlocking of gel and foam).

The handle 6 forming the gelatinous elastomer swabs of the invention can be made from various materials, such as: open cell foam, metal, wood, glass, carbon, plastic, rubber, ceramic, paper, straw, etc. The ends of the handle 6 can be lined with various substrate 4 material suitable for anchoring the gelatinous elastomer composition. The handle material can contain pores or channels 10 to interlock with the gelatinous elastomer composition to anchor the gelatinous elastomer swab head 2 to the handle 6. When foam is used as the handle material, a more firm material (such as materials suitable for the handle) can be used for support 8. The anchor (lining) material 4 can be heat sealed, heat welded, or glued to the ends of the handle 6 before dipping the ends of the handle 6 into the molten gelatinous elastomer composition. In forming the swabs, the molten gelatinous elastomer compositions can be casted, dipped, molded, or otherwise formed unto various handle substrate materials 4 lining the ends of the handle 6, such substrate materials 4 include: open cell materials, metals, ceramics, glasses, plastics, etc. Useful open-cell plastics include: polyamides, polyimides, polyesters, polyisocyanurates, polyisocyanates, polyurethanes, poly(vinyl alcohol), etc. Open-celled Plastic (foams) suitable for use with the compositions of the invention are described in "Expanded Plastics and Related Products", Chemical Technology Review No. 221, Noyes Data Corp., 1983, and "Applied Polymer Science", Organic Coatings and Plastic Chemistry, 1975. These publications are incorporated herein by reference.

Generally the molten gelatinous elastomer composition will adhere sufficiently to certain plastics (e.g. acrylic, ethylene copolymers, nylon, polybutylene, polycarbonate, polystyrene, polyester, polyethylene, polypropylene, styrene copolymers, and the like provided the temperature of the molten gelatinous elastomer composition is sufficient high to fuse or nearly fuse with the plastic (handle 6 material). In order to obtain sufficient adhesion to glass, ceramics, or certain metals, sufficient temperature is also required (e.g. above 250° F.). Commercial resins which can aid in adhesion to handle 6 materials (plastics, glass, and metals) may be added in minor amounts to the gelatinous elastomer composition, these resins include: Super Sta-tac, Nevtac, Piccotac, Escorez, Wingtack, Hercotac, Betaprene, Zonarez, Nirez, Piccolyte, Sylvatac, Foral, Pentalyn, Akron P, Regalrez, Cumar LX, Picco 6000, Nevchem, Piccotex, Kristalex, Piccolastic, LX-1035, and the like.

The invention is further illustrated by means of the following illustrative embodiments, which are given for purpose of illustration only and are not meant to limit the invention to the particular components and amounts disclosed.

EXAMPLE I

A comparison was made between a low viscosity poly(styrene-ethylene-butylene-styrene) triblock copolymer having styrene end block to ethylene and butylene center block ratio below the range between 31:69 to 40:60 and a high viscosity poly(styrene-ethylene-butylene-styrene) triblock copolymer of the invention. Three different triblock copolymers were melt blended separately with a paraffinic white petroleum oil. Table I below shows the physical properties obtain with respect to each of the different viscosity and styrene to ethylene and butylene ratio triblock copolymer oil-blends tested.

The properties were measured as follows: Tear Propagation (ASTM D 19938 modified), Cracking (ASTM D 518 Method B modified), Tensile Strength (ASTM D 412 modified), Ultimate elongation (ASTM D 412 modified), Tensile Set (ASTM D 412 Modified), Compression Set (ASTM D 395 modified), Snap Back, and Hand Kneading (60 seconds).

TABLE I

| Formulation | S/EB Ratio[1] | Weight Parts | | |
|---|---|---|---|---|
| | | A | B | C |
| SEBS[2] | 28:72 | 100 | | |
| SEBS[3] | 29:71 | | 100 | |
| SEBS[4] | 33:67 | | | 100 |
| Paraffinic oil[5] | | 400 | 400 | 400 |
| Stabilizer[6] | | 2.5 | 2.5 | 2.5 |
| Breaking strength[7], dyne/cm$^2$ | | $4 \times 10^5$ | $4 \times 10^5$ | $4 \times 10^6$ |
| Tear propagation[8], dyne/cm$^2$ | | $8 \times 10^4$ | $7 \times 10^4$ | $1 \times 10^6$ |
| Compression set[10] at 24 hours | | 81% (R) | 77% (R) | 0.0% |
| Rigidity, gram Bloom | | 1,536 | 1,520 | 360 |

[1]Styrene to ethylene and butylene ratio
[2]Shell Kraton G 1650 having a Brookfield viscosity of 1,500 cps as measured for a 20% weight solids solution in toluene at 25° C.
[3]Shell Kraton G 1652 having a Brookfield viscosity of 550 cps as measured for a 20% weight solids solution in toluene at 25° C.
[4]Shell Kraton G 1651 having a Brookfield viscosity of 2,000 cps as measured for a 20% weight solids solution in toluene at 25° C.
[5]ARCO prime 200,
[6]Irganox 1010,
[7]ASTM D 412 modified.
[8]ASTM D 1938 modified.
[9]ASTM D 412 modified.
[10]ASTM D 2395 modified,
(R) ruptured completely The results of Table I show drastically unacceptable poor properties of low viscosity triblock copolymers having styrene to ethylene and butylene ratios which are below the contemplated range of the instant invention.

EXAMPLE II

One hundred parts by weight of a high viscosity poly(styrene-ethylene-butylene-styrene) triblock copolymer (Shell Kraton G 1651) having a styrene end block to ethylene and butylene center block ratio of about 33:67 with 0.1 parts by weight of a stabilizer (Irrganox 1010) was melt blended with various quantities of a naphthenic oil (ARCO Tufflo 6024). Samples having the dimensions of 5 cm×5 cm×3 cm were cut and measured for gel rigidity on a modified Bloom gelometer as determined by the gram weight required to depress the gel a distance of 4 mm with a piston having a cross-sectional area of 1 cm$^2$. The average gel rigidity values with respect to various oil concentrations are set forth in Table II below.

TABLE II

| Oil per 100 parts of Triblock copolymer | Gel Rigidity, gram Bloom |
|---|---|
| 360 | 500 |
| 463 | 348 |
| 520 | 280 |
| 615 | 240 |
| 635 | 220 |
| 710 | 172 |
| 838 | 135 |
| 1,587 | 54 |

EXAMPLE III

Example II was repeated except about 980 parts oil was used and the gel rigidity found to about 101 gram Bloom. Other properties measured were: tensile strength at break about $4.4 \times 10^6$ dyne/cm2, elongation at break about 2,4470%, elasticity modulus about $3.5 \times 10^4$ dyne/cm2, and shear modulus about $3.7 \times 10^4$ dyne/cm$^2$. The tensile strength, elongation, elasticity modulus were measured with cross-head separation speed of 25 cm/minute at room temperature. The shear modulus was measured with a 1, 2, and 3 kilogram load at room temperature.

EXAMPLE IV

Example II was repeated except about 520 parts of a polybutene (Amoco Indopol H-300) was used and the gel rigidity found to be about substantially unchanged with respect to use of naphthenic oil alone.

EXAMPLE V

Example II was repeated except about 520 parts of a polypropene (Amoco C-60) was used and the gel rigidity found to be about substantially unchanged with respect to use of naphthenic oil alone.

EXAMPLE VI

Example II was repeated except about 520 parts of a polyterpene (Hercules Piccolyte S10) was used and the gel rigidity found to be about substantially unchanged with respect to use of naphthenic oil alone.

EXAMPLE VII

Example II was repeated except about 360 parts of a combined mixture of: 72 parts of a paraffinic oil (ARCO prime 200), 72 pars of a naphthenic oil (ARCO Tufflo 6014), 72 parts of a polybutene oligomer (Amoco Indopol H-200), 72 parts of a polypropane oligomer (Amoco Polypropene C-60), and 72 parts of a polyterpene oligomer (Hercules Piccolyte S10) was used and the gel rigidity found to be about substantially unchanged with respect to the use of naphthenic oil alone.

EXAMPLE VIII

Example III was repeated except 933 parts oil with 147 parts by weight of a high viscosity poly(styrene-ethylene-butylene-styrene) triblock copolymer containing 47 parts of a naphthenic process oil (Shell Kraton G 4609) having a styrene to ethylene and butylene ratio of about 33:67 was used and the physical properties were found to be about substantially unchanged with respect to the components used in Example III.

EXAMPLE IX

Example III was repeated except 933 parts oil with 147 parts by weight of a high viscosity poly(styrene-ethylene-butylene-styrene) triblock copolymer containing 47 parts of a paraffinic white petroleum oil (Shell Kraton G 4609) having a styrene to ethylene and butylene ratio of about 33:67 was used and the physical properties were found to be about substantially unchanged with respect to the components used in Example I.

EXAMPLE X

Example II was repeated except about 400 parts of oil was used and the properties measured were: tear propagation about $1.4 \times 10^6$ dyne/cm$^2$, no crack growth in 180° bend under 50 gram load for 5,000 hours at room temperature, tensile strength about $4 \times 10^6$ dyne/cm2, elongation at break about 1,700%, tensile set about 0% at 1,200% elongation, compression set about 0% when tested under 5,000 gram load for 24 hours, and 100% snap back recovery after extension to 1,200%.

Examples XI-XIV-j below illustrate other modes of practice contemplated.

EXAMPLE XI

The procedure of Example II is repeated and a poly(styrene-ethylene-butylene-styrene) triblock copolymer (characterized by a Brookfield Viscosity of a 20 weight percent solids solution in toluene at 25° C. of at least about 1,800 cps.) is used having a styrene end block to ethylene and butylene center block ratio of about 32:68 and the gel rigidity is found to be within the range of about 20 to about 800 gram Bloom.

EXAMPLE XII

The procedure of Example II is repeated and a poly(styrene-ethylene-butylene-styrene) triblock copolymer (characterized by a Brookfield Viscosity of a 20 weight percent solids solution in toluene at 25° C. of at least about 1,800 cps.) is used having a styrene end block to ethylene and butylene center block ratio of about 34:66 and the gel rigidity is found to be within the range of about 20 to about 800 gram Bloom.

EXAMPLE XIII

The procedure of Example II is repeated and a poly(styrene-ethylene-butylene-styrene) triblock copolymer (characterized by a Brookfield Viscosity of a 20 weight percent solids solution in toluene at 25° C. of at least about 1,800 cps.) is used having a styrene end block to ethylene and butylene center block ratio of about 36:64 and the gel rigidity is found to be within the range of about 20 to about 800 gram Bloom.

EXAMPLE XIV

The procedure of Example II is repeated and a poly(styrene-ethylene-butylene-styrene) triblock copolymer (characterized by a Brookfield Viscosity of a 20 weight percent solids solution in toluene at 25° C. of at least about 1,800 cps.) is used having a styrene end block to ethylene and butylene center block ratio of about 38:62 and the gel rigidity is found to be within the range of about 20 to about 800 gram Bloom.

EXAMPLE XIV-a

The procedure of Example II is repeated and a poly(styrene-ethylene-butylene-styrene) triblock copolymer (characterized by a Brookfield Viscosity of a 20 weight percent solids solution in toluene at 25° C. of at least about 1,800 cps.) is used having a styrene end block to ethylene and butylene center block ratio of about 31:69 and the gel rigidity is found to be within the range of about 10 to about 800 gram Bloom.

EXAMPLE XIV-b

The procedure of Example II is repeated and a poly(styrene-ethylene-butylene-styrene) triblock copolymer (characterized by a Brookfield Viscosity of a 20 weight percent solids solution in toluene at 25° C. of at least about 1,800 cps.) is used havjng a styrene end block to ethylene and butylene center block ratio of about 37:63 and the gel rigidity is found to be within the range of about 10 to about 800 gram Bloom.

EXAMPLE XIV-c

The procedure of Example II is repeated and a poly(styrene-ethylene-butylene-styrene) triblock copolymer (characterized by a Brookfield Viscosity of a 20 weight percent solids solution in toluene at 25° C. of at least about 1,800 cps.) is used having a styrene end block to ethylene and butylene center block ratio of about 19:81 and the gel rigidity is found to be within the range of about 10 to about 800 gram Bloom.

EXAMPLE XIV-d

The procedure of Example II is repeated and a poly(styrene-ethylene-butylene-styrene) triblock copolymer (characterized by a Brookfield Viscosity of a 20 weight percent solids solution in toluene at 25° C. of at least about 1,800 cps.) is used having a styrene end block to ethylene and butylene center block ratio of about 20:80 and the gel rigidity is found to be within the range of about 10 to about 800 gram Bloom.

EXAMPLE XIV-e

The procedure of Example II is repeated and a poly(styrene-ethylene-butylene-styrene) triblock copolymer (characterized by a Brookfield Viscosity of a 20 weight percent solids solution in toluene at 25° C. of at least about 1,800 cps.) is used having a styrene end block to ethylene and butylene center block ratio of about 38:62 and the gel rigidity is found to be within the range of about 10 to about 800 gram Bloom.

EXAMPLE XIV-f

The procedure of Example II is repeated and a poly(styrene-ethylene-butylene-styrene) triblock copolymer (characterized by a Brookfield Viscosity of a 20 weight percent solids solution in toluene at 25° C. of at least about 1,800 cps.) is used having a styrene end block to ethylene and butylene center block ratio of about 29:71 and the gel rigidity is found to be within the range of about 10 to about 800 gram Bloom.

EXAMPLE XIV-g

The procedure of Example II is repeated and a poly(styrene-ethylene-butylene-styrene) triblock copolymer (characterized by a Brookfield Viscosity of a 20 weight percent solids solution in toluene at 25° C. of at least about 1,800 cps.) is used having a styrene end block to ethylene and butylene center block ratio of about 26:74 and the gel rigidity is found to be within the range of about 10 to about 800 gram Bloom.

EXAMPLE XIV-h

The procedure of Example II is repeated and a poly(styrene-ethylene-butylene-styrene) triblock copolymer (characterized by a Brookfield Viscosity of a 20 weight percent solids solution in toluene at 25° C. of at least about 1,800 cps.) is used having a styrene end block to ethylene and butylene center block ratio of about 22:78 and the gel rigidity is found to be within the range of about 10 to about 800 gram Bloom.

EXAMPLE XIV-i

The procedure of Example II is repeated and a poly(styrene-ethylene-butylene-styrene) triblock copolymer (characterized by a Brookfield Viscosity of a 20 weight percent solids solution in toluene at 25° C. of at least about 1,800 cps.) is used having a styrene end block to ethylene and butylene center block ratio of about 25:75 and the gel rigidity is found to be within the range of about 10 to about 800 gram Bloom.

EXAMPLE XIV-j

The procedure of Example II is repeated and a poly(styrene-ethylene-butylene-styrene) triblock copolymer (characterized by a Brookfield Viscosity of a 20 weight percent solids solution in toluene at 25° C. of at least about 1,800 cps.) is used having a styrene end block to ethylene and butylene center block ratio of about 26:74 and the gel rigidity is found to be within the range of about 10 to about 800 gram Bloom.

EXAMPLE XV

Example II is repeated except the molten composition is casted onto a polyether, a polyester, a surlyn ionomer open cell sponge thereby displacing the air space within the sponge and the gel rigidity is found to be greater than about the sum of the combined rigidity of the composition and sponge alone.

EXAMPLE XVI

The composition of Example II is casted unto a SCOTFOAM® ⅛" thick: 5, 10, 15, 20, 25, 30, 35, 40, 45, 50, 60, 70, 80, 90, 100, and 200 ppi foam sheet.

EXAMPLE XVII

Example II is repeated. Swabs with representative substrate 4 materials and handle materials 6 as shown below are dipped into the molten compositions to form the gelatinous elastomer swabs of the invention.

| Substrate Material | Handle Material |
|---|---|
| 1. polyester | polypropylene |
| 2. closed cell foam | polypropylene |
| 3. 100 ppi open cell foam | polypropylene |
| 4. 20 ppi open cell foam | polyamides |
| 5. 25 ppi open cell foam | polyimides |
| 6. 30 ppi open cell foam | polyesters |
| 7. 35 ppi open cell foam | polyisocyanurates |
| 8. 40 ppi open cell foam | polyisocyanates |
| 9. 50 ppi open cell foam | polyurethanes |
| 10. 60 ppi open cell foam | nylon |
| 11. 70 ppi open cell foam | polybutylene |
| 12. 80 ppi open cell foam | polycarbonate |
| 13. 90 ppi open cell foam | polystyrene |
| 14. 100 ppi open cell foam | polyethylene |
| 15. 140 ppi open cell foam | polystyrene |
| 16. 200 ppi open cell foam | 200 ppi open cell foam |

The gelatinous elastomer swabs are use to clean a laser printer, a computer mouse, a computer keyboards, a copiers, a camera lenses, and other hard-to-clean surfaces.

While certain features of this invention have been described in detail with respect to various embodiments thereof, it will, of course, be apparent that other modifications can be made within the spirit and scope of the invention, and it is not intended to limit the invention to the exact details shown above except insofar as they are defined in the following claims.

What I claim is:

1. A reusable swab comprising;
(a) a handle;
(b) a gelatinous elastomer swab head, and
(c) means for attaching said swab head to one or both ends of said handle, said gelatinous elastomer swab head formed from a composition comprising:
(i) 100 parts by weight of a high viscosity triblock copolymer of the general configuration poly(styrene-ethylene-butylene-styrene);
(ii) from about 300 to about 1,600 parts by weight of a plasticizing oil; said composition characterized by a gel rigidity of from about 20 to about 800 gram Bloom.

2. A reusable swab according to claim 1, wherein said styrene to ethylene and butylene is of a ratio of from about 20:80 to about 40:60.

3. A reusable swab according to claim 1, wherein said styrene to ethylene and butylene is of a ratio of from about 30:70 to about 40:60.

4. A reusable swab according to claim 1, wherein said styrene to ethylene and butylene is of a ratio of from about 31:69 to about 40:60.

5. A reusable swab comprising:
(a) a handle, and
(b) a gelatinous elastomer swab head; wherein said swab head is interlocked with an open cell foam attached to one or both ends of said handle, said gelatinous elastomer swab head formed from a composition comprising:
(i) 100 parts by weight of a high viscosity triblock copolymer of the general configuration poly(styrene-ethylene-butylene-styrene);
(ii) from about 300 to about 1,600 parts by weight of a plasticizing oil; said composition characterized by a gel rigidity of from about 20 to about 800 gram Bloom.

6. A reusable swab according to claim 1 or 5, wherein said triblock copolymer is characterized by a Brookfield Viscosity of a 20 weight percent solid solution in toluene at 25° C. of at least about 1,800 cps.

* * * * *